United States Patent [19]

Paraschac et al.

[11] Patent Number: 5,797,938
[45] Date of Patent: Aug. 25, 1998

[54] SELF PROTECTING KNIFE FOR CURVED JAW SURGICAL INSTRUMENTS

[75] Inventors: Joseph F. Paraschac, Kettering; Kenneth S. Wales; Rudolph H. Nobis, both of Mason; Kip Rupp, New Richmond, all of Ohio

[73] Assignee: Ethicon Endo-Surgery, Inc., Cincinnati, Ohio

[21] Appl. No.: 751,898

[22] Filed: Nov. 18, 1996

Related U.S. Application Data

[63] Continuation of Ser. No. 545,977, Oct. 20, 1995, abandoned.
[51] Int. Cl.$^6$ .................................................. A61B 17/32
[52] U.S. Cl. ....................................... 606/167; 606/177
[58] Field of Search ........................ 606/37, 41, 51, 606/52; 227/180

[56] References Cited

U.S. PATENT DOCUMENTS

| | | | |
|---|---|---|---|
| 2,068,721 | 1/1937 | Wappler et al. | 606/46 |
| 2,676,406 | 4/1954 | Hoke | 30/342 |
| 4,655,216 | 4/1987 | Tischer | 606/51 |
| 5,290,287 | 3/1994 | Boebel et al. | 606/51 |
| 5,389,098 | 2/1995 | Tsuruta et al. | 606/41 |
| 5,445,638 | 8/1995 | Rydell et al. | 606/51 |
| 5,554,164 | 9/1996 | Wilson et al. | 606/167 |

FOREIGN PATENT DOCUMENTS

| | | |
|---|---|---|
| 0 623 316 A1 | 11/1994 | European Pat. Off. . |
| 0648475A1 | 4/1995 | European Pat. Off. . |
| WO 95/15124 | 6/1995 | WIPO . |

*Primary Examiner*—Michael Buiz
*Assistant Examiner*—Dapaja Shai
*Attorney, Agent, or Firm*—Bernard Shay

[57] ABSTRACT

An electrosurgical hemostatic instrument including a curved end effector. A preferred embodiment of the invention provides a bipolar endoscopic clamping, coagulation and cutting device. In this device, a substantially straight, axially flexible knife is used to cut tissue grasped by the jaws of the end effector. The end effector includes a knife channel which is wider than the knife. The knife may include sacrificial contact points adapted to contact the walls of the knife channel as the knife moves through the channel, protecting the cutting edges of the knife blade from damage.

7 Claims, 5 Drawing Sheets

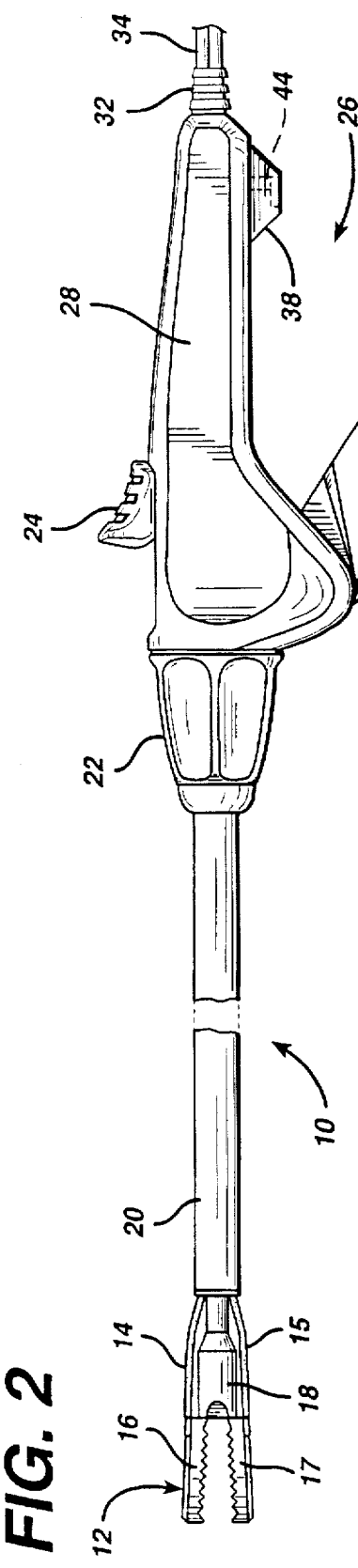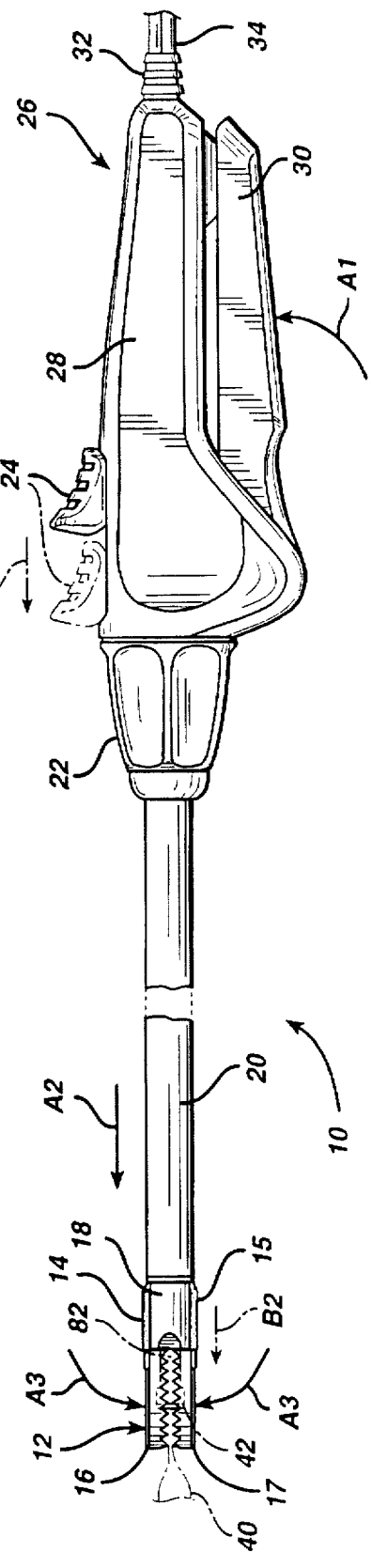

:# 5,797,938

SELF PROTECTING KNIFE FOR CURVED JAW SURGICAL INSTRUMENTS

This is a continuation of application Ser. No. 08/545,977, filed Oct. 20, 1995, now abandoned.

FIELD OF THE INVENTION

The present invention relates to an surgical instrument including a curved grasping, clamping or forceps type device and, in particular, to a surgical instrument including a curved clamping and cutting device with self protected knife.

BACKGROUND OF THE INVENTION

Electrosurgical hemostatic devices have been used for effecting improved hemostasis by heating tissue and blood vessels to cause coagulation or cauterization. Monopolar electrosurgical devices utilize one active electrode associated with the cutting or cauterizing instrument and a remote return or ground electrode which is usually attached externally to the patient. Thus in surgery utilizing monopolar instruments, electrical current passes from the active electrode, through the patient to the return electrode. In bipolar electrosurgical instruments both electrodes are included on the instrument and, generally, both electrodes are active. Thus, a typical bipolar instrument includes two or more electrodes which are charged to different electrical potentials. In bipolar instruments, the coagulating current flows through tissue positioned between the electrodes.

Electrical energy is used in medical instruments for hemostasis, that is to stop or slow bleeding in tissue. Application of electrical current in conjunction with pressure applied by the end effector of a surgical instrument results in a significant reduction in bleeding, and may be used to reduce bleeding prior to cutting tissue. The electrical current which passes through the tissue acts to heat the tissue. As the tissue is heated, it changes in color and texture. The experienced surgeon may, by looking for changes in the color or texture of the tissue around the end effector, determine when to turn off the current to the end effector. Once the tissue has been treated and the current turned off, the tissue grasped by the end effector may be cut, by, for example, advancing a knife blade through the end effector.

Bipolar forceps, being one type of bipolar electrosurgical instrument, have been used in various procedures for coagulating tissue. Generally bipolar forceps include two opposing jaws each connected to an output electrode of an electrical generator such that the opposing jaws are charged to different electrical potentials. Organic tissue being electrically conductive, when the jaws are used to grasp tissue the charged electrodes apply electrical current through the grasped tissue. Once the tissue has been treated to limit blood flow, a knife or other cutting instrument may be used to cut the tissue. In most such devices, the knife is positioned to travel through a knife channel in the instrument.

The use of curved end effectors in surgical instruments is particularly beneficial since a curved instrument may be designed to conform to the natural shape of the organ or tissue being treated. An electrosurgical device which includes a curved end effector with a knife adapted to travel through a knife channel is described and illustrated in U.S. patent application Ser. No. 08/395,732 filed Mar. 1, 1995 for a surgical instrument with "Expandable Cutting Element". In many curved end effectors which include a knife and a knife channel, the blade of the knife is protected by passing the knife through a relatively narrow knife channel. The narrow channel being less than twice the width of the knife and being adapted to conform the knife to the shape of the channel such that the cutting edge of the blade moves along the channel. Thus, a narrow channel provides particular advantages in a curved end effector. However, in certain circumstances it would be advantageous to use a curved end effector with a wide knife channel. Such a knife channel being at least three times the width of the knife, the sharpened blade at the leading edge of the knife would be expected to rub against at least a portion of the interior wall of the knife channel, potentially dulling the knife blade. It would, therefore, be advantageous to design a curved end effector including a wide knife channel wherein the cutting edge of the blade is protected as the blade advances through the knife channel.

In a curved end effector such as the end effector illustrated in FIGS. 1-5, it may be advantageous to build the end effector without insulating or lining the knife channel 82. The lack of insulation may not be a disadvantage since coagulation is generally complete before the knife is advanced through the knife channel. In addition, since the surgeon has control of the electrical current through operation of a footswitch or the like, the current may be switched off prior to advancing the knife through the knife channel. However, where a curved end effector is used with a substantially straight knife, the blade at the leading edge of the knife may become dull as it rubs against the sides of the knife channel. It would, therefore, be advantageous to design a knife wherein only a portion of the blade contacts the sides of the knife channel as it advances through the knife channel. Alternatively, it would be advantageous to design a knife blade which includes at least one rubbing spot adapted to rub against the sides of the knife channel.

SUMMARY OF THE INVENTION

In a curved end effector including a knife channel, a substantially straight axially flexible knife is adapted to move laterally from the proximal to the distal end of the knife channel. In one embodiment of the present invention, the width of the knife channel is at least three times the width of the knife blade. In a further embodiment of the present invention, the knife includes a sharpened blade at its leading edge adapted to cut tissue as the blade advances through the knife channel and the blade includes at least one sacrificial contact point adapted to contact the sides of the knife channel as the blade is advanced. In a further embodiment of the present invention, at least a portion of the knife blade is angled in a proximal to distal direction such that one or more at points of the leading edge of the knife blade comprise the sacrificial contact point. In a further embodiment of the present invention, the leading edge of the knife blade includes a plurality of sacrificial contact points.

In a further embodiment of the present invention, the knife blade travels through the knife channel making contact with the internal walls of the knife channel as it moves. Upon encountering a first wall of the knife channel, the knife bends to conform to the wall and, as the knife moves, the blade crosses the knife channel and contacts a second wall of the knife channel, cutting tissue as it moves.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

3

Figure 1:
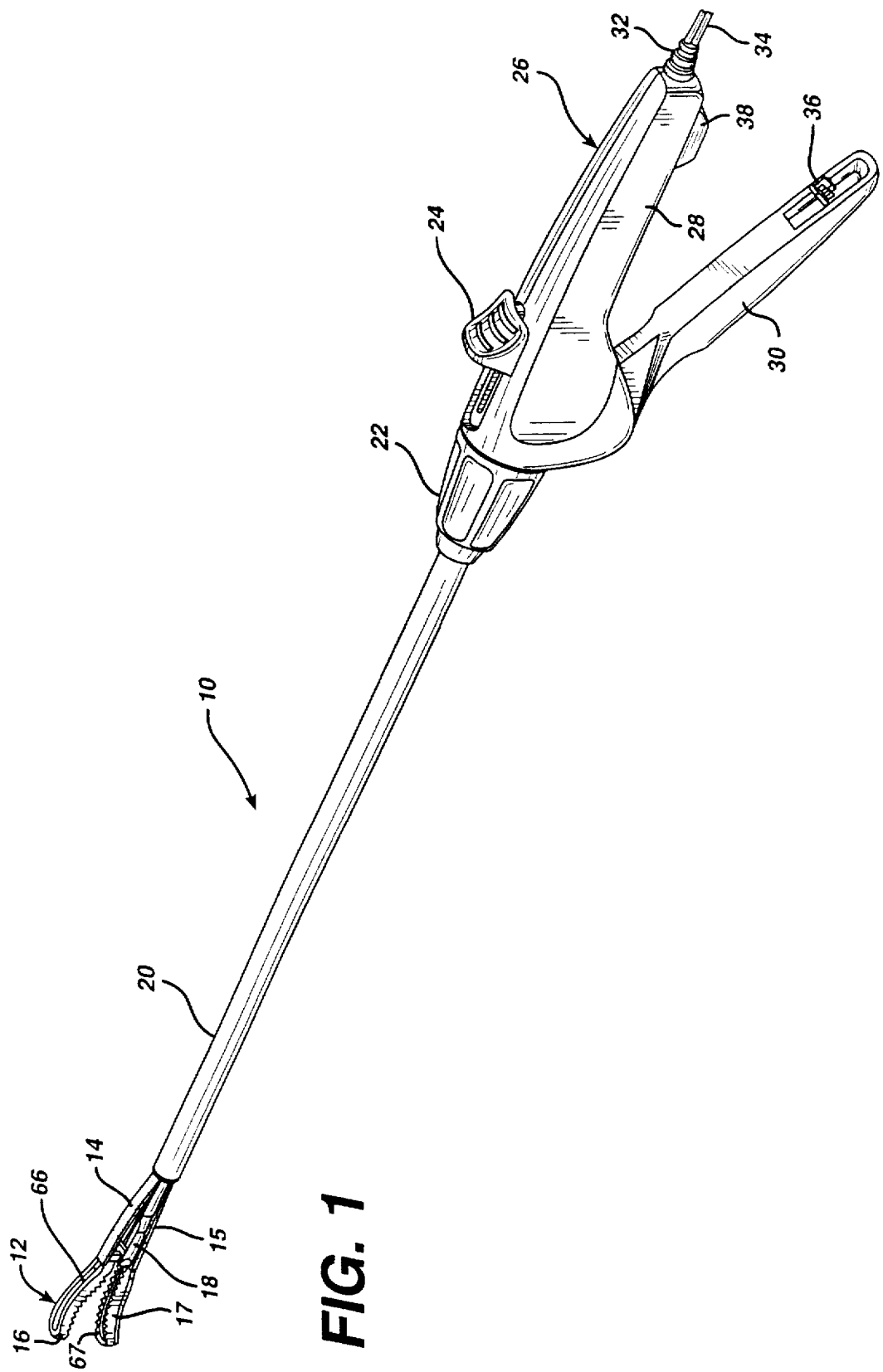
Figure 4:
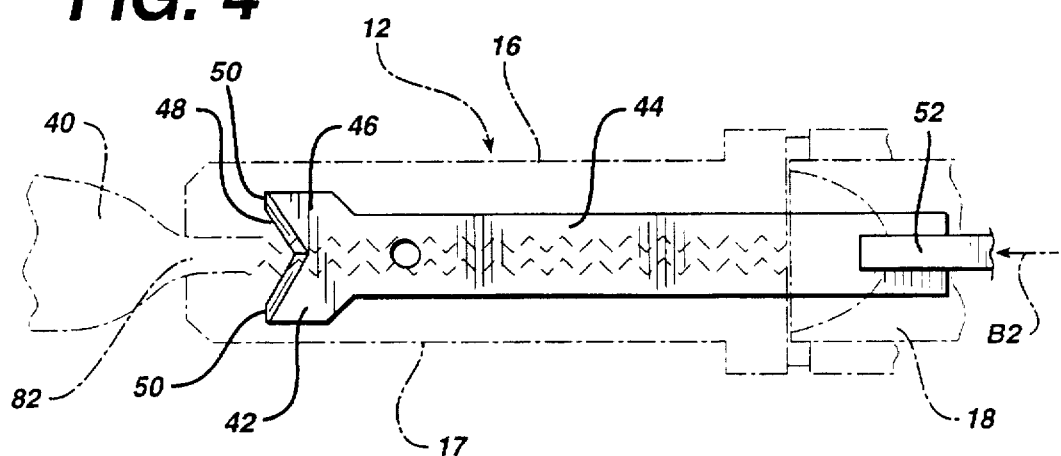

FIG. 1 is an elevated side view of a bipolar clamping, cutting and coagulating device including a curved end effector;

FIG. 2 is a side elevational view of the bipolar device illustrated in FIG. 1 shown in a first, unclamped position;

FIG. 3 is a side elevational view of the bipolar device illustrated in FIG. 1 shown in a second, clamped position;

FIG. 4 is a side view of a curved end effector jaw including a partially extended knife according to the present invention.

Figure 5:
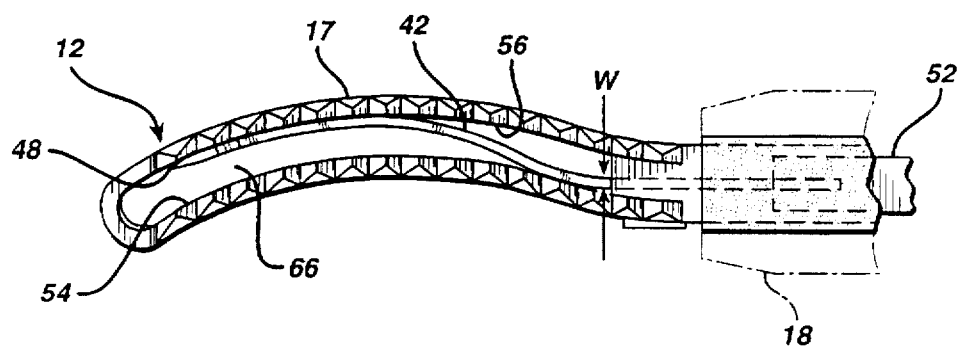

FIG. 5 is a bottom view of the curved bipolar end effector jaw illustrated in FIG. 4 including a partially extended knife according to the present invention.

Figure 6:
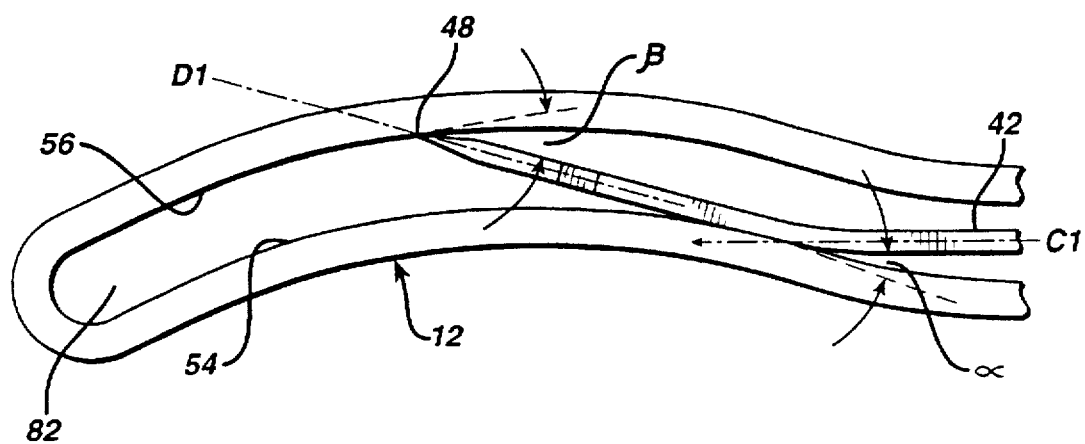

FIG. 6 is a partial view of a curved end effector according to the present invention illustrating the knife path in a curved end effector.

Figure 7:
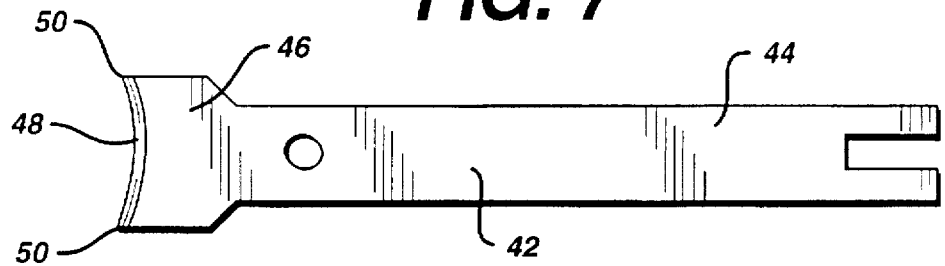
Figure 8:
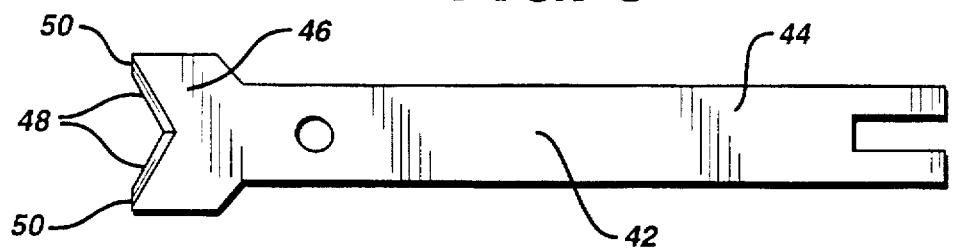
Figure 9:
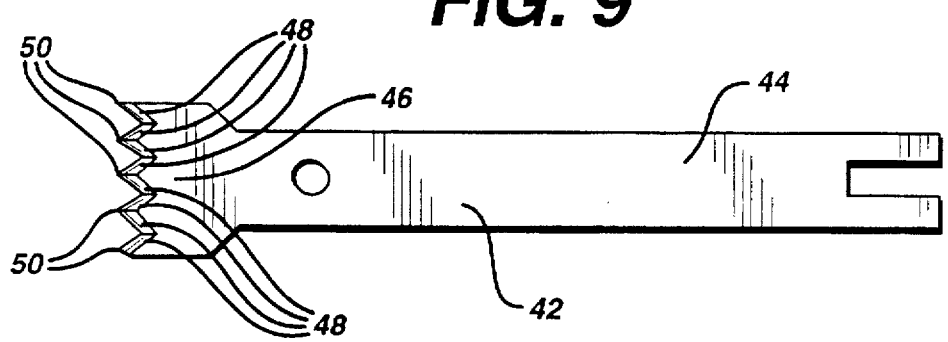
Figure 10:
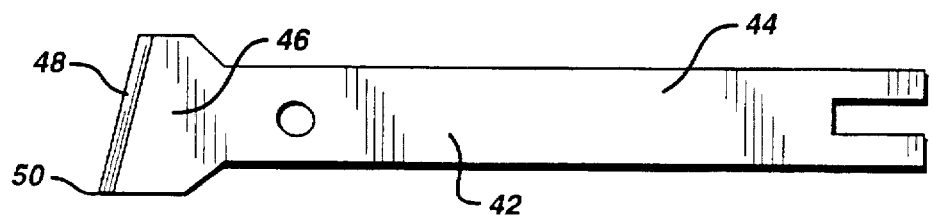

FIG. 7 illustrates a knife for use in a curved end effector according to the present invention FIG. 8 illustrates a knife for use in a curved end effector according to the present invention FIG. 9 illustrates a knife for use in a curved end effector according to the present invention FIG. 10 illustrates a knife for use in a curved end effector according to the present invention

DETAILED DESCRIPTION OF THE INVENTION

FIG. 1 is a perspective view of a bipolar cutting and coagulating device (e.g. a bipolar forceps) 10 according to the present invention. In bipolar forceps 10, upper jaw 16 and lower jaw 17 of end effector 12 are supported by upper wire form 14 and lower wire form 15. Wireforms 14 and 15 may also act as conductors supplying bipolar electrical energy to upper jaw 16 and lower jaw 17 respectively. Tissue stop 18 is positioned within closure tube 20 to prevent tissue from bypassing jaws 16 and 17 or contacting knife (not shown). Rotation knob 22 is affixed to closure tube 20 to cause rotation of closure tube 20 with respect to handle 26. Handle 26 includes knife button 24, grip 28 and trigger 30. Electrical cord 34 is connected to handle 26 through strain relief 32. Trigger latch 36 is positioned on trigger 30. Latch shield 38 is positioned on grip 28. Upper jaw 16 and lower jaw 17 of curved end effector 12 include upper knife channel 66 and lower knife channel 67 respectively.

As illustrated in FIGS. 2 and 3, bipolar forceps 10 have a first open position and a second, closed position. In the open position, illustrated in FIG. 2, trigger 30 is open, allowing closure tube 20 to move to its proximal position. With closure tube 20 in its proximal position, the spring force in wireforms 14 and 15 separate jaws 16 and 17 of the end effector 12. As illustrated in FIG. 3, movement of trigger 30 in direction A1, towards grip 28, forces closure tube 20 to move in direction A2, away from handle 26. As it moves, closure tube 20 forces wireforms 14 and 15 together which, in turn, forces jaws 16 and 17 to move in direction A3. When tissue 40 is positioned between jaws 16 and 17, closing trigger 30 causes jaws 16 and 17 to grip the tissue. Jaws 16 and 17 hold the tissue while it is being treated by, for example, applying high frequency bipolar energy. Alternatively, or after treatment of the tissue, knife 42 may be advanced into knife channel 82. Knife channel 82 is formed by upper knife channel 66 and lower knife channel 67 (Illustrated in FIG. 1). As illustrated in FIG. 3, knife 42 advances in direction B2 when knife button 24 is advanced in direction B1. Tissue stop 18 acts to shield knife 42 when knife 42 is in its retracted or proximal position.

4

FIG. 4 is an expanded view of the end effector illustrated in FIG. 3. wherein end effector 12 and tissue 40 are illustrated in shadow to more clearly illustrate knife 42. In FIG. 4, knife 42 has advanced through knife channel 82, cutting tissue 40 as it moves. Knife 42, includes flexible shaft 44, blade support 46 and cutting edge 48. In FIG. 4, cutting edge 48 includes a plurality of sacrificial contact points 50. Knife support 52 is connected to knife button 24 to drive knife 42 when knife button 24 is advanced as illustrated in FIG. 3.

FIG. 5 is a bottom view of jaw 17 of end effector 12 with knife 42 partially advanced into upper knife channel 66 which comprises the upper half of knife channel 82 (illustrated in FIG. 4). Knife 42, being flexible along its long axis, is advanced out of tissue stop 18 and into upper knife channel 66. Knife 42 moves through upper knife channel 66 until cutting edge 48, at the distal end of knife 42 encounters convex wall 54. Convex wall 54 forms one interior wall of upper knife channel 66. Knife 42, being flexible along its long axis, convex wall 54 deflects knife 42 towards concave wall 56 such that cutting edge 48 at the distal end of knife 42 encounters concave wall 56. As knife 42 advances beyond the point of contact with concave wall 56, leading edge 48 may move along wall 56 or, as illustrated in FIG. 4, flexible shaft 44 may conform to the surface of concave wall 56 and leading edge 48 move along a path substantially parallel to concave wall 56. Cutting edge 48 may include sacrificial contact points as illustrated in FIGS. 7-10. Since the width of the knife channel exceeds the width W of knife blade 42, the knife blade will not tend to conform to the shape of the knife channel until the spring forces within the knife force the knife blade to travel along concave wall 56.

As illustrated in FIG. 6, because end effector 12 is wider than knife 42 and curved while knife 42 is straight, advancing knife 42 will meet convex wall 54 of knife channel 82 at an angle $\chi$. If knife 42 continues to advance, it will meet concave wall 56 at an angle $\beta$. While the actual valve of $\chi$ and $\beta$ will be dependent upon the shape of the end effector and the shape of the knife channel, $\chi$ and $\beta$ will generally be greater than approximately five degrees. More particularly, the leading edge of the knife is particularly subject to damage where $\chi$ is greater than or equal to fifteen (15) degrees. Similarly, where $\beta$ is greater than or equal to fifteen degrees, the leading edge of the knife would be particularly subject to damage. Specifically, $\chi$ is an angle measured between a line tangential to the surface of convex wall 54 at the initial point of contact between the distal end of knife 46 and convex wall 54 and a line through the central axis C1 of knife 42. $\beta$ is an angle measured between a line tangential to the surface of concave wall 56 at the initial point of contact between the distal end of knife 42 and concave wall 56 and a line through the central axis D1 of knife 42.

The exact path taken by knife 42 as it travels through knife channel 82 will be a function of a number of variables, including, for example, the curvature of the end effector, the flexibility of the knife, the width of the knife channel, the length of the end effector, and the material in the knife channel. Thus, it may be that the knife will not bend to the degree illustrated in FIG. 5 or to the degree illustrated in FIG. 6 and may travel through the knife channel by, for example, glancing off convex wall 54 and scraping along convex wall 56. Whatever path the knife takes through the end effector, because the angle between the cutting edge a line tangential to and the interior walls of the knife channel is greater than approximately 5 degrees at the point of initial contact, it may be beneficial to design the knife blade to include sacrificial contact points at the end of the blade to protect the cutting edge as the distal end of the knife comes into contact with the interior walls of the knife channel. FIGS. 7-10 illustrate a number of knives which include such sacrificial contact points at their distal end.

The present invention is particularly well adapted to end effectors including knife channels which are significantly wider than the width of the knife and, in particular where the knife channel is more than 2.5 or 3 times the width of the knife.

In FIG. 7, knife 42 includes flexible shaft 44, blade support 46, cutting edge 48 and sacrificial contact points 50. In FIG. 7, sacrificial contact points are formed by curving cutting edge 48 in a distal to proximal direction such that sacrificial contact points 50 are the distal most points on knife 44.

In FIG. 8, knife 42 includes flexible shaft 44, blade support 46, cutting edge 48 and sacrificial contact points 50. In FIG. 8, sacrificial contact points 50 are formed by angling cutting edges 48 in a distal to proximal direction toward the center of blade 42 such that sacrificial contact points 50 are the most distal points on knife 42.

In FIG. 9, knife 42 includes flexible shaft 44, blade support 46, cutting edge 48 and sacrificial contact points 50. In FIG. 9, sacrificial contact points 50 are formed by angling cutting edges 48 in a distal to proximal direction such that sacrificial contact points 50 are the distal most points on knife 42.

In FIG. 10, knife 42 includes flexible shaft 44, blade support 46, cutting edge 48 and sacrificial contact point 50. In FIG. 10, a sacrificial contact point 50 is formed by angling cutting edge 48 in a distal to proximal direction such that sacrificial contact point 50 is at the distal most point of knife 42.

As illustrated in FIGS. 7, 9 and 10, sacrificial contact points 50 may comprise sharpened points which are an extension of cutting edge 48. Alternatively, as illustrated in FIG. 8, sacrificial contact points 50 may comprise flattened regions at the distal end of knife 42.

In FIGS. 1-4, U-shaped electrodes 16 and 17 have a substantially rectangular cross section. The use of a substantially rectangular cross section improves the structural strength of the jaws and, as a result, the clamping force which may be applied to the jaws. The rectangular cross section of the jaw also improves shielding of a knife blade as it moves along knife channel 282.

A generator, (not shown) may be used to provide electrosurgical energy to the bipolar electrodes 16 and 17. The generator is preferably an electrosurgical unit capable of providing bipolar energy. In the embodiment of FIG. 1, electrical energy is delivered through cord 34 to wires forms which are coupled to the electrodes. After electrosurgical energy is applied and the tissue is electrosurgically treated to a desired degree, a cutting element such as knife 42 may be advanced to cut the treated tissue as described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical instrument including an end effector wherein said end effector comprises:

first and second curved jaw members adapted to grasp tissue wherein said jaw members are curved along a proximal to distal axis of said instrument;

a curved knife channel within said jaw members wherein said knife channel is at least three times as wide as said knife;

an axially flexible knife adapted to move through said end effector from said proximal end to said distal end of said end effector wherein said knife includes a cutting edge at a distal end thereof, said cutting edge including at least one sacrificial contact point wherein said sacrificial contact point contacts said knife channel over a portion of its travel.

2. A surgical instrument according to claim 1 wherein at least a portion of said knife blade is angled in a distal to proximal direction such that said distal end of said cutting edge comprises said sacrificial contact point.

3. A surgical instrument according to claim 1 wherein said cutting edge includes a plurality of angled sections such that said cutting edge includes a plurality of sacrificial contact points at said distal end of said blade.

4. A surgical instrument according to claim 1 wherein said distal end of said knife contacts an interior wall of said end effector to form an angle between said interior wall and said knife blade.

5. A surgical instrument according to claim 1 wherein said distal end of said knife contacts said first interior wall of said knife channel at a first angle greater than five degrees and a second interior wall of said knife channel at a second angle greater than five degrees.

6. A surgical instrument comprising:

a proximal end including a handle;

a distal end including a curved end effector said end effector comprising:
a knife channel; and
jaws adapted to grasp tissue;

a knife adapted to move through said knife channel wherein said knife channel is at least 3 times as wide as said knife, wherein said knife comprises:

a shaft adapted to flex in the direction of curvature of said end effector; and a sharpened cutting edge at the distal end of said knife and a plurality of sacrificial points positioned to contact at least one interior wall of said knife channel as said knife moves through said channel.

7. A method of cutting tissue grasped between the jaws of a curved end effector using a substantially straight, axially flexible knife said method comprising the steps of:

a) moving said axially flexible knife through a first portion of said end effector until said knife contacts a first concave wall of said end effector at an interior angle greater than five degrees, said first wall forcing said knife to bend in a first direction toward a second convex wall of said knife channel;

b) moving said knife past said first wall, through said knife channel until said knife contacts said second wall at an interior angle greater than five degrees, said second wall bending said knife in a second direction substantially parallel to said second wall; and c) moving said knife along said second wall.

* * * * *